(12) United States Patent
Ko et al.

(10) Patent No.: US 12,209,272 B2
(45) Date of Patent: Jan. 28, 2025

(54) MULTIPLE ANALYSIS METHOD FOR AMPLICON BY USING FLUORESCENCE-BASED MULTIPLE MELTING ANALYSIS

(71) Applicant: NANOHELIX CO., LTD., Daejeon (KR)

(72) Inventors: Minsu Ko, Seoul (KR); Junsang Ko, Daejeon (KR); Hyejeong Yeom, Daejeon (KR)

(73) Assignee: NANOHELIX CO., LTD., Daejeon (KR)

( * ) Notice: Subject to any disclaimer, the term of this patent is extended or adjusted under 35 U.S.C. 154(b) by 979 days.

(21) Appl. No.: 17/182,705

(22) Filed: Feb. 23, 2021

(65) Prior Publication Data

US 2021/0180115 A1   Jun. 17, 2021

Related U.S. Application Data

(63) Continuation of application No. PCT/KR2018/012308, filed on Oct. 18, 2018.

(51) Int. Cl.
*C12Q 1/6806* (2018.01)
*C12Q 1/686* (2018.01)

(52) U.S. Cl.
CPC .......... *C12Q 1/6806* (2013.01); *C12Q 1/686* (2013.01); *C12Q 2521/101* (2013.01); *C12Q 2521/119* (2013.01); *C12Q 2525/204* (2013.01); *C12Q 2527/107* (2013.01); *C12Q 2563/107* (2013.01)

(58) Field of Classification Search
CPC ............ C12Q 1/6806; C12Q 2521/101; C12Q 2521/119; C12Q 2525/204; C12Q 2527/107; C12Q 1/6858; C12Q 1/6895; C12Q 1/6818; C12Q 2537/143; C12Q 2600/16; C12Q 1/686; C12Q 2525/161
See application file for complete search history.

(56) References Cited

U.S. PATENT DOCUMENTS

| | | | |
|---|---|---|---|
| 5,210,015 A | 5/1993 | Gelfand et al. | |
| 5,866,336 A * | 2/1999 | Nazarenko | C12Q 1/6844 435/6.12 |
| 6,117,635 A | 9/2000 | Nazarenko et al. | |
| 6,326,145 B1 | 12/2001 | Whitcombe et al. | |
| 2013/0224740 A1 * | 8/2013 | Thierry | C12Q 1/6886 435/6.12 |

FOREIGN PATENT DOCUMENTS

| | | |
|---|---|---|
| KR | 10-2009-0035303 A | 4/2009 |
| KR | 10-2012-0078193 A | 7/2012 |
| KR | 10-2016-0036906 A | 4/2016 |
| KR | 10-2016-0055055 A | 5/2016 |
| KR | 10-2016-0097193 A | 8/2016 |
| KR | 10-2016-0134982 A | 11/2016 |
| KR | 10-2017-0048092 A | 5/2017 |
| WO | 2013/133561 A1 | 9/2013 |

OTHER PUBLICATIONS

Liao et al, Nuc. Acids Res., vol. 41, article e76, pp. 1-11 and Supplementary Data, pp. 1-7, published online Jan. 18, 2013.*
Sanjay Tyagi et al., "Molecular Beacons: Probes that Fluoresce upon Hybridization", Nature Biotechnology, 1996, pp. 303-308, vol. 14.
International Search Report of PCT/KR2018/012308 dated Jun. 24, 2021 [PCT/ISA/210].

* cited by examiner

*Primary Examiner* — Narayan K Bhat
(74) *Attorney, Agent, or Firm* — Sughrue Mion, PLLC

(57) ABSTRACT

A method for multiplex analysis of amplification products using fluorescence-based multiple melting analysis is capable of analyzing multiple target nucleic acid sequences simultaneously in real time. A kit for performing the multiplex analysis contains target-specific primer/probe sets. The method and the kit allow a detection of multiple target nucleic acid sequences by a single polymerase chain reaction using a single fluorescence channel, thereby significantly reducing time and cost for multiplex nucleic acid detection. Therefore, the method and kit may be widely used in the companion diagnostic field in which multiple target nucleic acid genes need to be analyzed, the agricultural and livestock field in which multiple alleles need to be analyzed, and the clinical pathology field in which multiple infectious agents need to be analyzed simultaneously.

12 Claims, 8 Drawing Sheets

Specification includes a Sequence Listing.

SEQUENCE LISTING

```
<160> NUMBER OF SEQ ID NOS: 44

<210> SEQ ID NO 1
<211> LENGTH: 29
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: FAM fluorophore modification
<220> FEATURE:
<221> NAME/KEY: misc_feature
<222> LOCATION: (19)..(19)
<223> OTHER INFORMATION: BHQ1 modification

<400> SEQUENCE: 1
tagcgtaaaa tagaggagga catgataag                                      29

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
gaggaaaaaa catagcatgt ttc                                            23

<210> SEQ ID NO 3
<211> LENGTH: 45
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: FAM fluorophore modification
<220> FEATURE:
<221> NAME/KEY: misc_feature
<222> LOCATION: (21)..(21)
<223> OTHER INFORMATION: BHQ1 modification

<400> SEQUENCE: 3
gcgctggata ccctggacga gatcttacat ttggtttcac tgtta                    45

<210> SEQ ID NO 4
<211> LENGTH: 24
<212> TYPE: DNA
<213> ORGANISM: Artificial Sequence
<220> FEATURE:
<223> OTHER INFORMATION: Synthetic primer

<400> SEQUENCE: 4
cagtatgcta ataactcact aatt                                           24
```

```
<210> SEQ ID NO 5
<211> LENGTH: 41
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: FAM fluorophore modification
<220> FEATURE:
<221> NAME/KEY: misc_feature
<222> LOCATION: (21)..(21)
<223> OTHER INFORMATION: BHQ1 modification

<400> SEQUENCE: 5
cgcgccgcgc cccggccgcg caagcagcct catggaggta g                 41

<210> SEQ ID NO 6
<211> LENGTH: 22
<212> TYPE: DNA
<213> ORGANISM: Artificial Sequence
<220> FEATURE:
<223> OTHER INFORMATION: Synthetic primer

<400> SEQUENCE: 6
caacttgatt tcctgctgct at                                      22

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
gtagttataa ttattgggtt cacc                                    24

<210> SEQ ID NO 8
<211> LENGTH: 44
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: HEX fluorophore modification
<220> FEATURE:
<221> NAME/KEY: misc_feature
<222> LOCATION: (21)..(21)
<223> OTHER INFORMATION: BHQ1 modification

<400> SEQUENCE: 8
cgtcaggtaa gcgtgacgac tcactcctaa gatgccacat atcg              44

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
gaactctcac attagctaga aat                                     23

<210> SEQ ID NO 10
```

```
<211> LENGTH: 43
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: HEX fluorophore modification
<220> FEATURE:
<221> NAME/KEY: misc_feature
<222> LOCATION: (21)..(21)
<223> OTHER INFORMATION: BHQ1 modification

<400> SEQUENCE: 10
cgcccggcgg gcgcggcgca gtgttggttg tgagttgata ctg              43

<210> SEQ ID NO 11
<211> LENGTH: 41
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Cy5 fluorophore modification
<220> FEATURE:
<221> NAME/KEY: misc_feature
<222> LOCATION: (21)..(21)
<223> OTHER INFORMATION: BHQ2 modification

<400> SEQUENCE: 11
ccgcggggcc cgcccggcga cagccgatca gatagatccc t                41

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
caatgtggat tgtgaaggtg a                                      21

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
gttcaagaat ttggagaatc aat                                    23

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
gcaacatcgg actgaaaggt                                        20

<210> SEQ ID NO 15
<211> LENGTH: 23
<212> TYPE: DNA
<213> ORGANISM: Artificial Sequence
```

```
<220> FEATURE:
<223> OTHER INFORMATION: Synthetic primer

<400> SEQUENCE: 15
ctgtaaagat tgaactgcca aat                                              23

<210> SEQ ID NO 16
<211> LENGTH: 22
<212> TYPE: DNA
<213> ORGANISM: Artificial Sequence
<220> FEATURE:
<223> OTHER INFORMATION: Synthetic primer

<400> SEQUENCE: 16
ggaaccacca ccgtttaaat aa                                               22

<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
tggtatgtca cattctgtac ga                                               22

<210> SEQ ID NO 18
<211> LENGTH: 43
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Cy5 fluorophore modification
<220> FEATURE:
<221> NAME/KEY: misc_feature
<222> LOCATION: (21)..(21)
<223> OTHER INFORMATION: BHQ1 modification

<400> SEQUENCE: 18
ggagacatca gatacagagt gtcggttatt gcaggtgata ttt                        43

<210> SEQ ID NO 19
<211> LENGTH: 43
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: TexasRed modification
<220> FEATURE:
<221> NAME/KEY: misc_feature
<222> LOCATION: (21)..(21)
<223> OTHER INFORMATION: BHQ1 modification

<400> SEQUENCE: 19
ccgtacctta gagacagcgt ggatgcttgc aagagggat att                         43

<210> SEQ ID NO 20
<211> LENGTH: 21
<212> TYPE: DNA
<213> ORGANISM: Artificial Sequence
<220> FEATURE:
<223> OTHER INFORMATION: Synthetic primer
```

<400> SEQUENCE: 20
tcttgatatg gcacccatcc a    21

<210> SEQ ID NO 21
<211> LENGTH: 21
<212> TYPE: DNA
<213> ORGANISM: Artificial Sequence
<220> FEATURE:
<223> OTHER INFORMATION: Synthetic primer

<400> SEQUENCE: 21
cagtcattgg ggtcaatgcc a    21

<210> SEQ ID NO 22
<211> LENGTH: 22
<212> TYPE: DNA
<213> ORGANISM: Artificial Sequence
<220> FEATURE:
<223> OTHER INFORMATION: Synthetic primer

<400> SEQUENCE: 22
gcaagaacca ggaccatgtg ct    22

<210> SEQ ID NO 23
<211> LENGTH: 22
<212> TYPE: DNA
<213> ORGANISM: Artificial Sequence
<220> FEATURE:
<223> OTHER INFORMATION: Synthetic primer

<400> SEQUENCE: 23
tgtcagtcat gataatccaa gg    22

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
catgtttaga aactgcaatg gc    22

<210> SEQ ID NO 25
<211> LENGTH: 42
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: HEX fluorophore modification
<220> FEATURE:
<221> NAME/KEY: misc_feature
<222> LOCATION: (21)..(21)
<223> OTHER INFORMATION: BHQ1 modification

<400> SEQUENCE: 25
cgtcaggtaa gcgtgacgac tgacgtcata gcaacaacta cg    42

<210> SEQ ID NO 26
<211> LENGTH: 23
<212> TYPE: DNA
<213> ORGANISM: Artificial Sequence
<220> FEATURE:
<223> OTHER INFORMATION: Synthetic primer

```
<400> SEQUENCE: 26
caccaactca tcttaccttt aac                                           23

<210> SEQ ID NO 27
<211> LENGTH: 21
<212> TYPE: DNA
<213> ORGANISM: Artificial Sequence
<220> FEATURE:
<223> OTHER INFORMATION: Synthetic primer

<400> SEQUENCE: 27
cagaaggtgc ccatccatgt t                                             21

<210> SEQ ID NO 28
<211> LENGTH: 22
<212> TYPE: DNA
<213> ORGANISM: Artificial Sequence
<220> FEATURE:
<223> OTHER INFORMATION: Synthetic primer

<400> SEQUENCE: 28
ctacacctac tttcttcgtc aa                                            22

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
taagggacat gacgggtcag                                               20

<210> SEQ ID NO 30
<211> LENGTH: 22
<212> TYPE: DNA
<213> ORGANISM: Artificial Sequence
<220> FEATURE:
<223> OTHER INFORMATION: Synthetic primer

<400> SEQUENCE: 30
tgtctgcact gacttcttca tc                                            22

<210> SEQ ID NO 31
<211> LENGTH: 21
<212> TYPE: DNA
<213> ORGANISM: Artificial Sequence
<220> FEATURE:
<223> OTHER INFORMATION: Synthetic primer

<400> SEQUENCE: 31
atccatcatc cgaaggatgt g                                             21

<210> SEQ ID NO 32
<211> LENGTH: 43
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Cy5 fluorophore modification
<220> FEATURE:
<221> NAME/KEY: misc_feature
<222> LOCATION: (21)..(21)
```

<223> OTHER INFORMATION: BHQ2 modification

<400> SEQUENCE: 32
ggagacatca gatacagagt gactagaata tggaaccta gag    43

<210> SEQ ID NO 33
<211> LENGTH: 21
<212> TYPE: DNA
<213> ORGANISM: Artificial Sequence
<220> FEATURE:
<223> OTHER INFORMATION: Synthetic primer

<400> SEQUENCE: 33
tgctagtaca gatgaggagg t    21

<210> SEQ ID NO 34
<211> LENGTH: 22
<212> TYPE: DNA
<213> ORGANISM: Artificial Sequence
<220> FEATURE:
<223> OTHER INFORMATION: Synthetic primer

<400> SEQUENCE: 34
ttcaacatgc atgatgcaaa gc    22

<210> SEQ ID NO 35
<211> LENGTH: 24
<212> TYPE: DNA
<213> ORGANISM: Artificial Sequence
<220> FEATURE:
<223> OTHER INFORMATION: Synthetic primer

<400> SEQUENCE: 35
cgacattctt gtttgatatt tctt    24

<210> SEQ ID NO 36
<211> LENGTH: 22
<212> TYPE: DNA
<213> ORGANISM: Artificial Sequence
<220> FEATURE:
<223> OTHER INFORMATION: Synthetic primer

<400> SEQUENCE: 36
gatgaaggat cttggtgttg ct    22

<210> SEQ ID NO 37
<211> LENGTH: 21
<212> TYPE: DNA
<213> ORGANISM: Artificial Sequence
<220> FEATURE:
<223> OTHER INFORMATION: Synthetic primer

<400> SEQUENCE: 37
gatgatatgc tgattgctgc c    21

<210> SEQ ID NO 38
<211> LENGTH: 41
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: TexasRed modification
<220> FEATURE:
<221> NAME/KEY: misc_feature

```
<222> LOCATION: (21)..(21)
<223> OTHER INFORMATION: BHQ2 modification

<400> SEQUENCE: 38
gcgggccgcg ggcgccgcca ctcgacggcg acctgacttg t                         41

<210> SEQ ID NO 39
<211> LENGTH: 41
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: TexasRed modification
<220> FEATURE:
<221> NAME/KEY: misc_feature
<222> LOCATION: (21)..(21)
<223> OTHER INFORMATION: BHQ2 modification

<400> SEQUENCE: 39
ggagacatca gatacagagt gtcgacggcg acctgacttg t                         41

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
gcattggaga cgaactgacg                                                 20

<210> SEQ ID NO 41
<211> LENGTH: 19
<212> TYPE: DNA
<213> ORGANISM: Artificial Sequence
<220> FEATURE:
<223> OTHER INFORMATION: Synthetic primer

<400> SEQUENCE: 41
tggcgggcgg gagacgttc                                                  19

<210> SEQ ID NO 42
<211> LENGTH: 42
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: HEX fluorophore modification
<220> FEATURE:
<221> NAME/KEY: misc_feature
<222> LOCATION: (21)..(21)
<223> OTHER INFORMATION: BHQ1 modification

<400> SEQUENCE: 42
ggagacatta gatatagagt gactggcttg ctgccgtatc ca                        42

<210> SEQ ID NO 43
<211> LENGTH: 42
<212> TYPE: DNA
<213> ORGANISM: Artificial Sequence
<220> FEATURE:
<223> OTHER INFORMATION: Synthetic primer
<220> FEATURE:
```

```
<221> NAME/KEY: misc_feature
<222> LOCATION: (1)..(1)
<223> OTHER INFORMATION: HEX fluorophore modification
<220> FEATURE:
<221> NAME/KEY: misc_feature
<222> LOCATION: (21)..(21)
<223> OTHER INFORMATION: BHQ1 modification

<400> SEQUENCE: 43
cgcccggcgg gcgcggcgca gactggcttg ctgccgtatc ca                42

<210> SEQ ID NO 44
<211> LENGTH: 43
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Cy5 fluorophore modification
<220> FEATURE:
<221> NAME/KEY: misc_feature
<222> LOCATION: (21)..(21)
<223> OTHER INFORMATION: BHQ2 modification

<400> SEQUENCE: 44
gcgggccgcg ggcgccgcca cactagaata tggaacccta gag               43
```

MULTIPLE ANALYSIS METHOD FOR AMPLICON BY USING FLUORESCENCE-BASED MULTIPLE MELTING ANALYSIS

CROSS REFERENCE TO RELATED APPLICATIONS

This application is a continuation of PCT/KR2018/012308 filed on Oct. 18, 2018, claiming priority based on Korean Patent Application No. 10-2018-0116472 filed on Sep. 28, 2018.

SEQUENCE LISTING

The content of the electronically submitted sequence listing, file name: SequenceListing as filed.txt; size: 10,981 bytes; and date of creation: Feb. 18, 2021, filed herewith, is incorporated herein by reference in its entirety.

TECHNICAL FIELD

The present disclosure relates to a method for multiplex analysis of amplification products using fluorescence-based multiple melting analysis, and more particularly to a method for multiplex analysis of polymerase chain reaction products, which is capable of simultaneously analyzing multiple target nucleic acids using a single fluorescence channel through fluorescence-based melting temperature analysis.

BACKGROUND ART

Real-time polymerase chain reaction (PCR) is a molecular biology technique that amplifies a specific gene fragment of a full-length gene, which has a known nucleotide sequence, by DNA polymerase, and examines and isolates the gene. Real-time PCR measures amplification products in real time, reduces cross-contamination, and enables more accurate quantitative analysis. This real-time polymerase chain reaction has become one of the essential techniques in research and testing in the fields of biochemistry, molecular biology, medicine and clinical pathology.

Real-time polymerase chain reaction (PCR) has the same basic principle as common polymerase chain reaction, but differs in that it can quantitatively monitor polymerase chain reaction products in real time. Real-time PCR may be classified into: an intercalator method in which a fluorophore is inserted into an amplification product to display fluorescence (e.g., SYBR™ green); and a probe method in which a fluorophore reacts only with a specific amplification product to display fluorescence (e.g., TAQMAN®). In the former case, a non-specific amplification product cannot be distinguished, and hence a method of analyzing the melting temperature of the product, that is, melting temperature analysis, is used as an auxiliary. The probe method has advantages in that it has relatively high accuracy because it selectively detects an amplification product, and in that it can simultaneously detect 4 to 6 target nucleic acids using different types of fluorescence. Due to these advantages, the probe method is widely used in diagnostic procedures in the field of clinical pathology.

The reason why the probe-based diagnostic method capable of multiplex analysis is mainly used is that the number of genotypes that need to be analyzed at the same time has been increasing in recent years. The most commonly used TAQMAN® method uses a probe labeled with a fluorophore and a quencher at both ends, and is a method using the cleavage of the probe by 5'-3' nuclease activity of DNA polymerase, and this method is currently the most mainstream (U.S. Pat. No. 5,210,015).

In addition, methods using labeled primers include a molecular beacon-based method (Tyagi & Kramer, Nature Biotechnology, 1996), a sunrise primer method (U.S. Pat. No. 6,117,635), a scorpion primer method (U.S. Pat. No. 6,326,145), and the like. In these methods, when a target is amplified using the stem-loop structure of the primer, the structure changes and the fluorophore and the quencher are separated from each other to emit fluorescence.

The disadvantage of real-time PCR that is currently in use is the limited possibility of multiplex analysis. Current real-time PCR technology uses a fluorescent dye as a means of detecting an amplification reaction. Since the types of fluorescent dyes that can be used are limited due to overlapping wavelengths, that is, only one target nucleic acid can be analyzed in one fluorescence channel, the number of samples that can be analyzed simultaneously is limited to 4 to 6 (6-plex).

International Patent Publication No. WO2013133561 discloses a real-time polymerase chain reaction method which can simultaneously analyze 2 to 3 target nucleic acids in a single fluorescence channel using a PTOCE (Probing & Tagging Oligonucleotide Cleavage and Extension) method in which a probe that binds selectively to a target nucleic acid DNA and a melting curve analysis method are applied at the same time. This method has the advantage of significantly increasing the number of target nucleic acids that can be analyzed, compared to the conventional method of analyzing one target nucleic acid using one type of fluorescence. However, this method has many difficulties in designing primers, because the number of primers and oligonucleotides used in analysis reaches several dozens and interference between them should be minimized.

In recent years, there has been a continuous increase in genotypes that need to be analyzed at the same time for the development of genotype-specific drugs, such as companion diagnostic drugs, or determination of the presence or absence of multiple allelic markers. In addition, in the field of diagnosis of infectious diseases, there has been an increased need to simultaneously diagnose as many pathogens as possible. Therefore, there has been an urgent need to develop a new method for multiplex analysis of nucleic acid amplification products, which is capable of amplifying and detecting a larger number of DNAs in a single reaction and in which primer design is relatively simple.

DISCLOSURE

Technical Problem

The present invention has been made to meet the above-described technical requirements, and an object of the present invention is to provide a method for multiplex analysis of amplification products using fluorescence-based multiple melting analysis, which is capable of detecting multiple targets simultaneously using a single fluorescence channel by labeling primers complementary to target nucleic acid genes with a fluorophore and a quencher and introducing a melting temperature control sequence for inducing various melting temperatures.

Another object of the present invention is to provide a primer design method and a melting temperature analysis method, which are required for multiplex analysis of nucleic acid amplification products.

Still another object of the present invention is to provide a kit for multiplex analysis of nucleic acid amplification products, which is capable of detecting multiple targets simultaneously using a single fluorescence channel.

Yet another object of the present invention is to provide a method of analyzing genotypes using fluorescence-based multiple melting analysis, which provides a fast, simple and automated identification method capable of analyzing varieties simultaneously using a plurality of markers.

Technical Solution

In the present invention, fluorescence-based multiple melting analysis (FMMA method) was developed to achieve the above-described objects. That is, it was made possible to analyze a number of different melting temperatures simultaneously in a single fluorescence channel. To this end, in the present invention, a new type of "FMMA probe" was developed, which was designed to be involved directly in nucleic acid amplification and to be used also for analysis of the melting temperatures of amplification products, unlike conventional probes that are not involved in the formation of amplification products.

One aspect of the present invention is directed to a method for multiplex analysis of amplification products using fluorescence-based multiple melting analysis, the method including steps of:

a) preparing target-specific fluorescence-based multiple melting analysis (FMMA) probe/primer sets which each include an FMMA probe (having a structure of 5'-R-T-Q-C-3') and a non-labeled primer, wherein R is a fluorescent label, T is a melting temperature control sequence for inducing different temperatures of different amplification products, Q is a quencher, C is a sequence complementary to a target nucleic acid sequence, and each FMMA probe/primer is designed to produce each amplification product having a different melting temperature;

b) amplifying multiple target nucleic acids in a sample containing one or more target nucleic acids by a nucleic acid polymerase chain reaction using the target-specific FMMA probe/primer sets obtained in the preceding step; and c) performing melting temperature analysis on amplification products.

In the present invention, adjustment of the melting temperature of each FMMA probe/primer in the target-specific FMMA probe/primer sets is designed such that the melting point of the amplification product is distinguished by controlling the length and GC content of the amplification product and the length and GC content of the melting temperature control sequence.

In the present invention, the FMMA probes/primers may be designed such that the adjacent melting temperatures of the amplification products have a difference of 2° C. or higher, preferably 4° C. or higher.

In the present invention, the length of the melting temperature control sequence (T) is 10 to 30 bp, and the length of the amplification product is 50 to 300 bp.

The step of performing melting temperature analysis includes steps of: obtaining a melting curve by measuring fluorescence generated by melting the amplification product while increasing the temperature thereof; and obtaining a melting peak curve from the melting curve.

Another aspect of the present invention is directed to a method for genotyping using fluorescence-based multiple melting analysis, the method including steps of: a) preparing allele-specific FMMA probe-primer sets which each include an FMMA probe (having a structure of 5'-R-T-Q-C-3') and a non-labeled primer, wherein R is a fluorescent label, T is a melting temperature control sequence for inducing different temperatures of different amplification products, Q is a quencher, C is a sequence complementary to a target nucleic acid sequence, and each FMMA probe/primer is designed to produce each amplification product having a different melting temperature;

b) amplifying multiple target nucleic acids in a sample containing one or more target nucleic acids by a nucleic acid polymerase chain reaction using the allele-specific FMMA probe/primer sets obtained in the preceding step; and c) detecting alleles in the sample by performing melting temperature analysis on amplification products.

Advantageous Effects

The present invention provides the possibility of multiplexing so that a plurality of target nucleic acids may be amplified in a single real-time PCR reaction and analyzed in a single fluorescence channel, by using target-specific FMMA probe/primer sets composed of a plurality of FMMA probes/primers including different melting temperature control sequences.

According to the FMMA method of the present invention, it is possible to analyze multiple target nucleic acids simultaneously, thereby reducing time and cost for performing real-time PCR.

The method for genotyping using fluorescence-based multiple melting analysis according to another aspect of the present invention enables more efficient and economical testing by reducing time and labor required for testing through simplification of a PCR process for identifying rice varieties.

BEST MODE

Figure 1A:
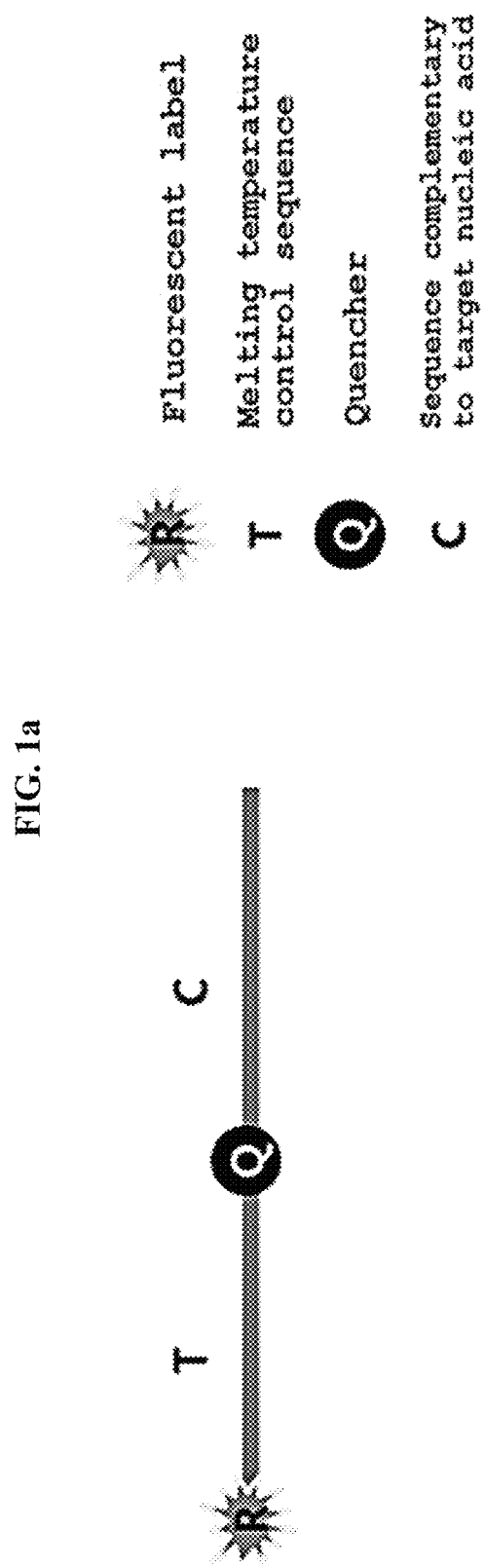
FIGS. 1a and 1b are schematic views illustrating the principle of fluorescence-based multiple melting analysis (FMMA) of the present invention.

The present invention will be described in more detail below with reference to examples. These examples are intended for illustrative purposes only, but are not intended to limit the scope of the present invention.

As used herein, the term "target nucleic acid" or "target nucleic acid gene" refers to a nucleic acid sequence to be finally detected. The target nucleic acid gene may be a portion of a gene, a regulatory sequence, genomic DNA, cDNA, RNA including mRNA, microRNA and rRNA, or others. A nucleic acid molecule that is the target nucleic acid gene may be double-stranded or single-stranded. Where the nucleic acid as a starting material is double-stranded, it is preferred to render the two strands into a single-stranded or partially single-stranded form. Where an mRNA is used as a starting material, a reverse transcription step is necessary prior to amplification.

As used herein, the term "primer" refers to an oligonucleotide that may act as a point of initiation of DNA synthesis under conditions in which synthesis of a primer extension product complementary to the template nucleic acid strand is induced. The conditions include the presence of nucleotides and an inducing agent such as DNA polymerase at a suitable temperature and pH. The primer is preferably a single-stranded oligodeoxyribonucleotide. The primers that are used in the present invention may include naturally occurring dNMPs (i.e., dAMP, dGMP, dCMP and dTMP), modified nucleotides or non-naturally occurring nucleotides. The primers may also include ribonucleotides.

As used herein, the term "FMMA probe" refers to an oligonucleotide, its complements, or fragments thereof, which is used to detect identical, allelic or related nucleic acid sequences. FMMA probes may include oligonucleotides which have been attached to a detectable label or fluorescent molecule. FMMA probes are involved directly in nucleic acid amplification and used also for analysis of melting temperatures, unlike conventional probes that are not involved in the formation of amplification products.

As used herein, the term "melting temperature" is defined as the temperature at which 50% of the double-stranded DNAs in a population are dissociated into single-stranded DNAs. The melting temperature has various values depending on the GC content and length of DNA, thermodynamic factors, salt concentrations, etc., and is determined by melting analysis.

As used herein, the term "melting analysis" refers to a process of analyzing the change in fluorescence that appears when increasing temperature from low temperature after completion of PCR reaction. Through this process, the melting temperature is determined.

As used herein, the term "melting curve" or "melting peak curve" as used herein refers to a graph showing the change in fluorescence (RFU) depending on the temperature (T) obtained during melting analysis. The melting curve or the melting peak curve is plotted with temperature on the x-axis and fluorescence on the y-axis. The "melting peak curve" is a curve expressed as a negative value $(-d(RFU)/dT)$ obtained by first-order differentiation of the obtained melting curve, and the temperature at the peak is the melting temperature.

The present inventors have developed a method of inducing various melting temperatures by adjusting the GC content of the melting temperature control sequence of the real-time PCR primer and the length of the amplification product.

In general, in order to detect a plurality of target nucleic acids simultaneously, a conventional amplification curve analysis method using real-time PCR uses fluorophores to detect the target nucleic acids in a sample, and thus only one fluorophore may be used as a label for each nucleic acid to be detected. In addition, in current systems for detecting fluorophores, the number of fluorescence channels that can be analyzed simultaneously is limited to 4 to 6 types, and thus multiplex detection is limited. However, the method for multiplex analysis of amplification products using fluorescence-based multiple melting analysis according to the present invention is characterized in that a primer complementary to a target nucleic acid is labeled with a fluorescent label and a quencher, and a melting temperature control sequence for inducing various melting temperatures is introduced to the primer, whereby multiple targets may be detected using a single fluorescence channel. The method of the present invention may be used to analyze multiple nucleic acids, alleles, or the presence or absence of a certain nucleotide sequence in a sample.

One aspect of the present invention is directed to a method for multiplex analysis of amplification products using fluorescence-based multiple melting analysis, the method including steps of:

a) preparing target-specific FMMA probe/primer sets which each include an FMMA probe (having a structure of 5'-R-T-Q-C-3') and a non-labeled primer, wherein R is a fluorescent label, T is a melting temperature control sequence for inducing different temperatures of different amplification products, Q is a quencher, C is a sequence complementary to a target nucleic acid sequence, and each FMMA probe/primer is designed to produce each amplification product having a different melting temperature;

b) amplifying multiple target nucleic acids in a sample containing one or more target nucleic acids by a nucleic acid polymerase chain reaction using the target-specific FMMA probe/primer sets obtained in the preceding step; and c) performing melting temperature analysis on amplification products.

Figure 1B:
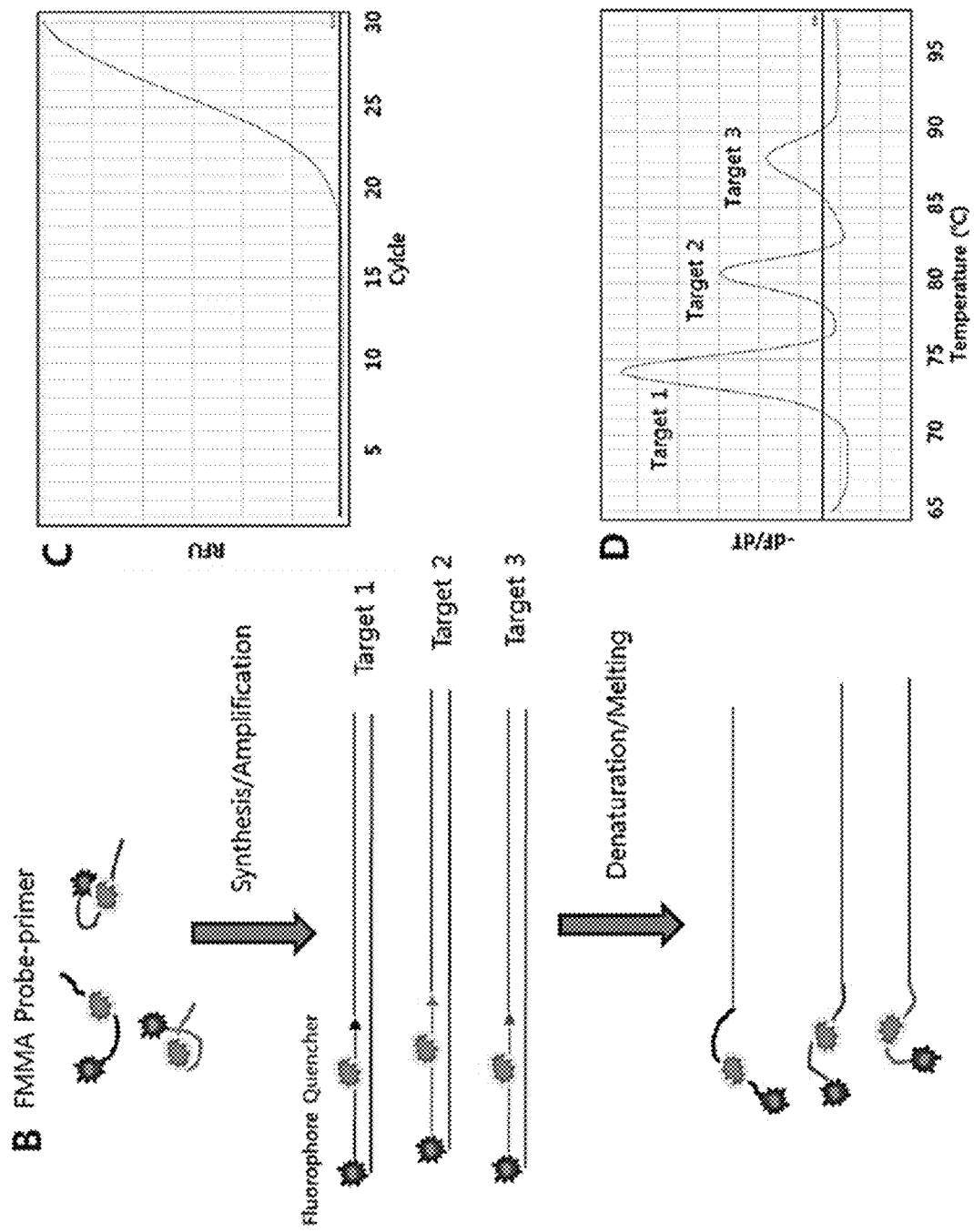

FIGS. 1a and 1b are schematic views illustrating the principle of fluorescence-based multiple melting analysis (FMMA) of the present invention.

Each step of the method of the present invention will now be described in more detail with reference to FIGS. 1a and 1b.

a) Step of Designing FMMA Probe/Primer Sets that Induces Various Melting Temperatures Referring to FIG. 1a, in order to perform multiplex analysis according to the method of the present invention, FMMA probe/primer sets are first prepared, which each include an FMMA probe (having a structure of 5'-R-T-Q-C-3') and a non-labeled primer. In this case, R is a fluorescent label, T is a melting temperature control sequence for inducing different melting temperatures of different amplification products, Q is a quencher, C is a sequence complementary to a target nucleic acid sequence, and each FMMA probe/primer is designed to produce each amplification product having a different melting temperature.

Referring to FIG. 1b, the above-designed FMMA probe/ primer set having the structure 5'-R-T-Q-C-3' does not generate a fluorescent signal in the absence of a target nucleic acid, but generates fluorescence as shown in C of FIG. 1b when amplification occurs due to the presence of the target nucleic acid in the reaction solution. In a conventional real-time PCR process, this amplification curve is caused by a single target, but in the present invention, the amplification curves of all the targets labeled with the same fluorophore appear as a single amplification curve.

When the melting temperature analysis is performed to determine whether or not amplification of such multiple targets has occurred, it is possible to analyze a plurality of targets having different melting temperatures ($T_m$) values as shown in D of FIG. 1b. In this case, the melting temperature of the amplification product has various values depending on the GC content of the melting temperature control sequence and the length of the amplification product.

Each melting temperature control sequence (T) in the target-specific FMMA probe/primer sets is designed such that the melting point of each amplification product is distinguished by adjusting the length and GC content of the amplification product and the length and GC content of the melting temperature control sequence. The target-specific FMMA probes-primers are preferably configured such that the difference between adjacent melting temperatures is 2° C. or higher, more preferably 4° C. or higher, in order to distinguish between amplification products. The target-specific FMMA probes/primers having the same fluorescent label may be configured such that the difference between adjacent temperatures of the amplification products is 2° C. or higher, 3° C. or higher, 4° C. or higher, 5° C. or higher, 6° C. or higher, 7° C. or higher, 8° C. or higher, 9° C. or higher, or 10° C. or higher.

In the present invention, the melting temperature control sequence (T) is 10 to 30 bp in length. The GC content of the target-specific FMMA probe/primer set including the melting temperature control sequence is 0 to 100%, more preferably 20 to 90%.

In the present invention, a fluorescent label (R) is used as a signal generating means for generating a signal indicating the presence of a target nucleic acid. A fluorescent label that may be used in the present invention may be selected from the group consisting of 5-carboxyfluorescein(FAM™), TET™, 2'7'-dimethoxy-4'5'-dichloro-6-carboxyfluorescein (JOE™), VIC™, HEX™, 6-carboxy-X-rhodamine (ROX™), N,N,N',N'-tetramethyl-6-carboxyrhodamine (TAMRA™), CYDYE™(CY2™, CY3™, CY3.5™, CY5™, and CY5.5™), OREGON GREEN™(OREGON GREEN™ 488, OREGON GREEN™ 500, OREGON GREEN™ 514), CAL RED™, RED 640®, and TEXAS RED®, but is not necessarily limited thereto.

Additional non-limiting examples of the fluorescent label include, but are not limited to, quantum dots, ALEXA FLUOR™ dye, AMCA, BODPY-BODIPY™ 630/650, BODIPY™ 650/665, BODIPY™-FL, BODIPY™-R6G, BODIPY™-TMR, BODIPY™-TRX, CASCADEBLUE™, fluorescein, 6-JOE™, OREGON GREEN™ 488, OREGON GREEN™ 500, OREGON GREEN™ 514, PACIFIC BLUE™, REG, phycobiliprotein, phycoerythrin, allophycocyanin, RHODAMINE GREEN™, RHODAMINE RED™, ROX™, TAMRA™, TET™, and tetramethylrhodamine. Fluorophores have different excitation and emission wavelengths depending on their type, and their usage is also different. The characteristics of the target fluorophores are summarized in Table 1 below.

TABLE 1

| Filter | Excitation wavelength | Emission wavelength | Fluorophores |
|---|---|---|---|
| 1 | 490 | 520 | FAM ™ (fluorescein amidit), SYBR ™ Green |
| 2 | 520 | 550 | JOE ™ (6-carboxy-4',5'-dichloro-2',7'-dimethoxyfluoresein), VIC ™, HEX ™ (hexachlorofluoresein) TET ™ (tetrachlorofluoresein) |
| 3 | 550 | 580 | NED ™, TAMRA ™, CY3 ™ |
| 4 | 580 | 610 | TEXAS RED ®, ROX ™ (carboxy-X-rhodamine), RED610 |
| 5 | 640 | 670 | CY5 ™, RED670 |

As used herein, the term "quencher" refers to a substance that reduces fluorescence intensity by absorbing light generated by the fluorescent label. The quencher that is used in the present invention may be selected from the group consisting of N,N,N',N'-tetramethyl-6-carboxyrhodamine (TAMRA™), 4-(4'-dimethylaminophenylazo) benzoic acid (DABCYL), ECLIPSE®, NFQ, BLACK HOLE QUENCHER® (BHQ®), Deep Dark Quencher (DDQ), QSY®, BLACKBERRY™ Quencher, QXL®, IOWA BLACK® FQ, IOWA BLACK® RQ, and IRDYE® QC-1, but is necessarily limited thereto. The quencher may be selected in consideration of the fact that the range in which the fluorescence intensity is reduced by the quencher differs depending on the type of quencher. Suitable fluorescent label-quencher pairs are disclosed in various literatures as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ EDITION (Academic Press, New York, 1971); Griffiths, Color and Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996); U.S. Pat. Nos. 3,996,345 and 4,351,760.

b) PCR Amplification of Multiple Target Nucleic Acids

Multiple target nucleic acids in a sample containing one or more target nucleic acids are amplified by polymerase chain reaction using the target-specific FMMA probe-primer sets obtained in the preceding step.

In the present invention, the amplification reaction of the target nucleic acid/FMMA probe complex may be performed using reagents necessary for amplification, for example, suitable amounts of DNA polymerase, DNA polymerase cofactor ($Mg^{2+}$), buffer solution, dNTPs (dATP, dCTP, dGTP and dTTP) and water ($dH_2O$), in addition to the primer set of the present invention. The buffer solution may further contain, but is not limited to, suitable amounts of TRITON™ X-100, dimethyl sulfoxide (DMSO), TWEEN20®, NONIDET™ P40, PEG 6000, formamide and bovine serum albumin (BSA).

When the polymerization reaction is performed, excessive amounts of components necessary for the reaction are preferably provided to a reactor. "The excessive amounts of components necessary for the amplification reaction" means such amounts that the amplification reaction is not substantially limited by concentrations of the components. Cofactors such as $Mg^{2+}$, and dATP, dCTP, dGTP and dTTP are preferably provided to the reaction mixture such that a desired degree of amplification may be achieved.

Nucleic acid polymerase that may be used in the present invention may be an RNA-dependent RNA-polymerase, an RNA-dependent DNA-polymerase, a DNA-polymerase, or an RNA-polymerase.

Non-limiting examples of the nucleic acid polymerase include *Thermus aquaticus* (Taq) polymerase, *Thermus thermophilus* (Tth) polymerase, *Thermococcus litoralis* (Tli or VENT™) polymerase, *Pyrococcus furiosus* (Pfu) polymerase, DEEPVENT™ polymerase, *Pyrococcus woosii* (Pwo) polymerase, *Bacillus sterothermophilus* (Bst) polymerase, *Sulfolobus acidocaldarius* (Sac) polymerase, Tac polymerase, *Thermus flavus* (Tfl/Tub) polymerase, *Thermus*

*ruber* (Tru) polymerase, *Thermus brockianus* (DYNAZYME™) polymerase, *Thermotoga neapolitana* (Tne) polymerase, *Thermotoga maritima* (Tma) polymerase, Tsp polymerase, *Methanobacterium thermoautotrophicum* (Mth) polymerase, Phi29 polymerase, Klenow polymerase, T7 polymerase, or KOD DNA polymerase. A preferred example of the nucleic acid polymerase is Taq polymerase.

One PCR reaction may consist of 10 to 100 "cycles" of denaturation and synthesis of a DNA molecule. In a preferred embodiment, the temperature at which denaturation is done in a thermocycling amplification reaction is about 90° C. to more than 95° C., more preferably 92° C. to 94° C. Preferred thermocycling amplification methods include polymerase chain reactions involving from about 10 to about 100 cycles, more preferably from about 25 to about 50 cycles, and peak temperatures from about 90° C. to more than 95° C., more preferably 92° C. to 94° C.

In the annealing step of the process of amplifying the target DNA using the target-specific FMMA probe/primer set, the target-specific FMMA probe-primer set is annealed to the complementary strand of the target nucleic acid, and when the target DNA is amplified during the amplification process, an amplification curve signal (fluorescence) is generated. Unlike conventional probes, the FMMA probe of the present invention is a probe that is involved directly in nucleic acid amplification, and thus the mechanism of action thereof is different from those of other types of probes that show fluorescence by binding to the target DNA. That is, the FMMA probe of the present invention displays fluorescence by forming a portion of the amplification product. In the melting temperature analysis process, when the double strands are separated into single strands, fluorescence decreases, making melting temperature analysis possible. Thus, unlike a conventional method in which a probe alone is separated from a target nucleic acid and the melting temperature thereof, the FMMA probe of the present invention forms a portion of the amplification product.

c) Analysis of Melting Temperature of Each Amplification Product

Melting temperature analysis is performed on the amplification products. The step of analyzing the melting temperature includes a step of obtaining a melting curve by measuring fluorescence generated by melting each amplification product while increasing the temperature thereof, and then obtaining a melting peak curve from the melting curve.

Each target-specific FMMA probe is specific to the target nucleic acid sequence, and two or more probes having the same label are present in each set. The amplification products of the target-specific FMMA probe/primer sets having the same label are distinguished from each other because they have a melting temperature ($T_m$) that differ from each other by a melting temperature of 2° C. or higher, more preferably 2° C. or higher. Therefore, through melting temperature analysis, products amplified by different target-specific FMMA probes/primers having the same label may be distinguished from each other.

Another aspect of the present invention is directed to a method for genotyping using fluorescence-based multiple melting analysis. The method of the present invention includes steps of: a) preparing a plurality of allele-specific probe/primer sets, which each have a structure of 5'-R-T-Q-C-3' and each include an FMMA probe-primer, wherein R is a fluorescent label capable of detecting whether or not the allele is amplified, T is a melting temperature control sequence for inducing different temperatures of different amplification products, Q is a quencher, C is a sequence complementary to a target nucleic acid sequence, and each FMMA probe/primer is designed to produce each amplification product having a different melting temperature; and b) amplifying multiple target nucleic acids in a sample containing one or more target nucleic acids by a nucleic acid polymerase chain reaction using the target-specific FMMA probe/primer set obtained in the preceding step. After completion of the amplification, the allele in the sample is detected by performing melting temperature analysis on the amplification products.

In this case, in a real-time PCR system such as Biorad CFX96, a graph showing the temperature on the x-axis and fluorescence signal intensity on the y-axis is plotted using the built-in analysis software. Thereafter, the analysis software differentiates the fluorescence signal intensity on the y-axis with respect to temperature to facilitate visual identification, and then plots a graph with negative values on the y-axis, that is, a graph with temperature on the x-axis and −d(RFU)/dT values on the y-axis. After a differential curve of the change in the fluorescence level with the change in the melting temperature ($T_m$) is obtained as described above, genotyping is performed according to the presence or absence of a peak representing each genotype.

Figure 2:
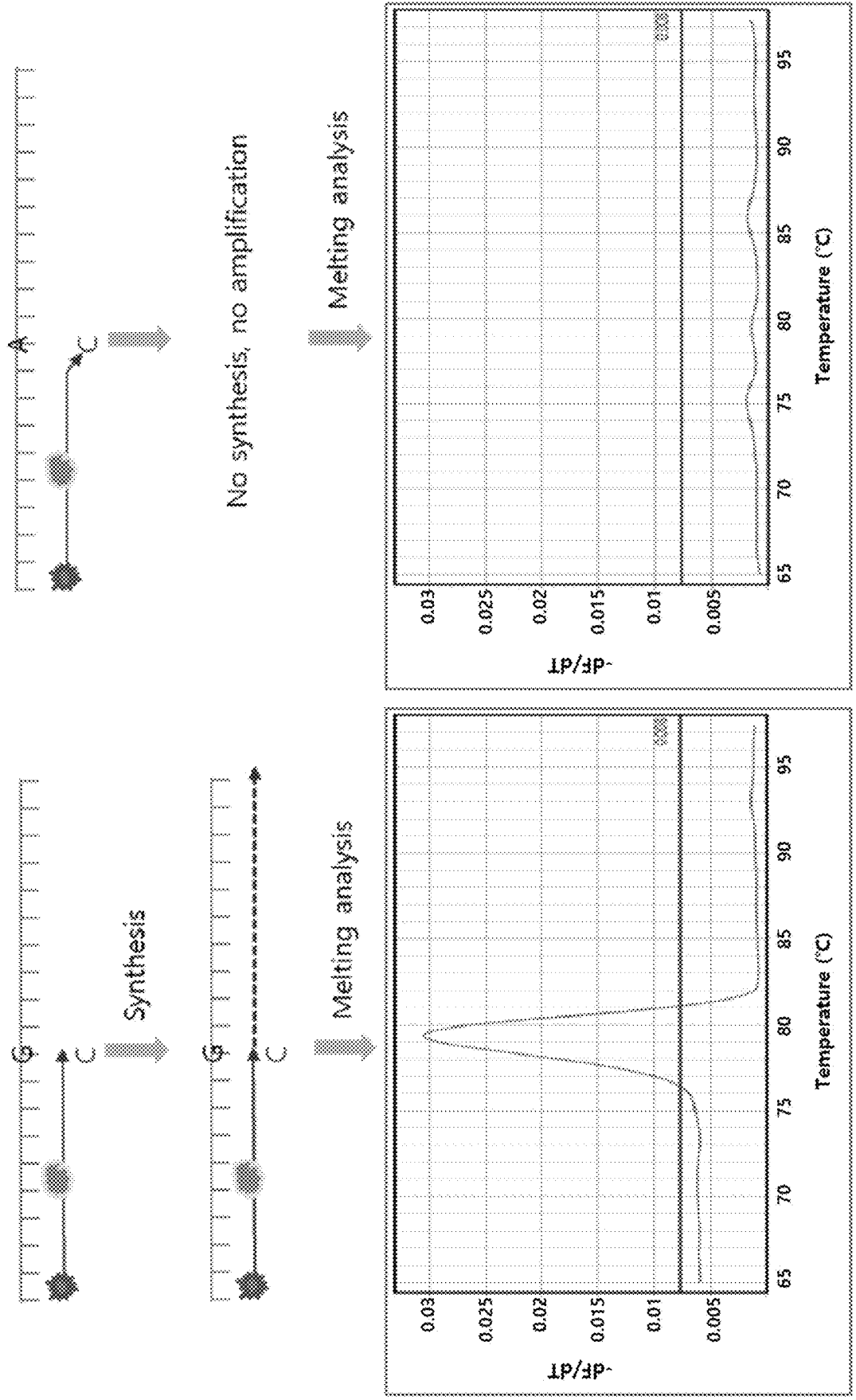
FIG. 2 is a schematic view illustrating allele-specific FMMA for rice variety identification, performed in an Example.

FIG. 2 is a schematic view illustrating allele-specific FMMA for rice variety identification. In the present invention, an allele-specific SNP marker is used, and the SNP marker is a marker whose 3' end nucleotides exactly match any one allele, but are substituted with a nucleotide that mismatches other specific alleles. In the present invention, in order to be able to simultaneously analyze multiple target allele-specific SNP markers using a single fluorescent label, the amplification product length and the melting temperature control sequence are designed such that the amplification products have 2 or 3 different melting temperatures.

Referring to FIG. 2, the target-specific FMMA probe/primer set according to a marker for rice variety identification according to the present invention coincides with a specific allele representing SNP. Thus, the FMMA probe hybridizes specifically to the template DNA for the alleles that match complementarily, but the FMMA probe does not hybridize to a non-specific allele. In this case, since the FMMA probe is labeled with a detectable means such as a fluorescent label, the SNP type of the product amplified by PCR can be identified. The presence or absence of a product amplified by PCR using the allele-specific marker for rice variety identification can be easily analyzed using melting curve analysis.

The measured melting temperature ($T_m$) on the melting curve shows a melting peak when the FMMA probe of each of the target-specific FMMA probe-primer sets is consistent with the nucleotide at the SNP position of each target gene and thus amplification occurs. Therefore, comparison of the $T_m$ value makes it possible to detect nucleotide variation at the SNP position.

As used herein, the term "nucleotide variation" refers to various alleles appearing in the same gene. In other words, the term "nucleotide variation" encompasses both wild-types and mutants. Therefore, detection of nucleotide variation may be expressed by genotyping or detection of an allele.

As used herein, the term "genetic variation" refers to a phenomenon occurring due to an allele, single nucleotide polymorphism (SNP), mutation, or a combination thereof. In this case, the allele refers to genes that exhibit different characters while existing at the same locus on a chromosome, or genes having different nucleotide sequences located at the same locus on homologous chromosomes.

Still another aspect of the present invention is directed to a kit for multiplex detection of target nucleic acids using fluorescence-based multiple melting analysis, the kit including the target-specific FMMA probe/primer sets of the present invention.

The kit of the present invention includes a) target-specific FMMA probe/primer sets, which each include an FMMA probe (having a structure of 5'-R-T-Q-C-3') and a non-labeled primer, wherein R is a fluorescent label, T is a melting temperature control sequence for inducing different temperatures of different amplification products, Q is a quencher, C is a sequence complementary to a target nucleic acid sequence, and each FMMA probe/primer is designed to produce each amplification product having a different melting temperature.

According to another preferred embodiment of the present invention, the kit may optionally include reagents necessary for nucleic acid amplification, for example, buffer, DNA polymerase (e.g., thermostable DNA polymerase isolated from *Thermus aquaticus* (Taq), *Thermus thermophilus* (Tth), *Thermus filiformis, Thermis flavus* or *Thermococcus literalis*), a DNA polymerase cofactor, and dNTPs.

The kit of the present invention may consist of a number of separate configurations including the above-described reagent components. In addition, the kit of the present invention may further include a user's guide describing conditions under which the optimum reaction is performed.

The present invention provides a kit for identification of allele-specific rice varieties, the kit including the allele-specific FMMA probe-primer sets of the present invention as described above. The kit for identification of allele-specific rice varieties according to the present invention can identify rice varieties using multiplex allele-specific multiplex polymerase chain reaction.

The kit for identification of allele-specific rice varieties according to the present invention establishes a real-time PCR method that uses at least 15 marker sets for rice variety identification at the same time, and is highly advantageous in that it can minimize necessary testing time and labor by significantly simplifying the PCR process.

Hereinafter, the present invention will be described in more detail with reference to examples. However, the following examples serve merely to illustrate the present invention, and the scope of the present invention is not limited to the following examples.

Example 1

Rice Variety Identification Using Allele-Specific FMMA
1-1. Design for Primers for FMMA For multiple-target analysis, which is a characteristic of the present invention, SNPs (single nucleotide polymorphisms) on several alleles were applied for the identification of rice varieties to be analyzed. For the identification of rice varieties, the presence or absence of about 20 SNP markers was examined, and the varieties were determined according to the patterns thereof.

As shown in FIG. 2, an FMMA primer specific to the SNP site of each type of marker gene was designed to show a melting peak at a certain temperature when the amplification product has the genotype of interest.

Primers used for rice variety analysis were designed based on the information on genetic markers for rice variety identification and nucleotide sequences thereof, provided by the National Agricultural Products Quality Management Service. That is, the primers were designed such that whether the presence or absence of the SNP corresponding to each genetic marker could be determined based on whether amplification occurred. The primers were designed such that the length of each amplification product and the melting temperature control sequence changed so that the amplification products had 2 or 3 different melting temperatures, making it possible to analyze multiple markers using a single fluorescent label. The sequences of the primers used in this Example and the sizes, GC contents and melting temperatures of amplification products are shown in Table 2 below.

TABLE 2

| Fluorescent label | Allele | Name | Nucleotide sequence | PCR product size (bp) | PCR product GC content (%) | PCR product T$_m$ (° C.) |
|---|---|---|---|---|---|---|
| FAM ™ | BR09 | BRa09-F3(T-In)-3[FAM ™] | [FAM ™]TAGCGTAAAATAGAGGAGG[BHQ1]ACATGAtAAG (SEQ ID NO: 1) | 52 | 36.5 | 72.5 |
| | | BR09-(T)R2 | GAGGAAAAAACATAGCATGTTTC (SEQ ID NO: 2) | | | |
| FAM ™ | BR06 | BR06-F(FAM ™) | [FAM ™]GCGCTGGATACCCTGGACGAG[BHQ1]ATCTTACATTTGGTTTCACTGTTA (SEQ ID NO: 3) | 239 | 33.5 | 80.0 |
| | | BRq06-R | CAGTATGCTAATAACTCACTAATT (SEQ ID NO: 4) | | | |
| FAM ™ | BR01 | BR01-F(FAM ™) | [FAM ™]CGCGCCGCGCCCCGGCCGCGC[BHQ1]AAGCAGCCTCATGGAGGTAG (SEQ ID NO: 5) | 308 | 42.2 | 87.0 |
| | | BRq01-R | CAACTTGATTTCCTGCTGCTAT (SEQ ID NO: 6) | | | |
| HEX ™ | BR02 | BRc02-F | GTAGTTATAATTATTGGGTTCACC (SEQ ID NO: 7) | 134 | 31.3 | 78.5 |
| | | BRa02-RL1(HEX ™) | [HEX ™]CGTCAGGTAAGCGTGACGACT[BHQ1]CACTCCTAAGATGCCACATAtCG (SEQ ID NO: 8) | | | |

TABLE 2-continued

| Fluorescent label | Allele | Name | Nucleotide sequence | PCR product size (bp) | PCR product GC content (%) | PCR product T$_m$ (° C.) |
|---|---|---|---|---|---|---|
| HEX ™ | BR04 | BRq04-F | GAACTCTCACATTAGCTAGAAAT (SEQ ID NO: 9) | 305 | 32.5 | 84.0 |
| | | BRa04-RL1(HEX ™) | [HEX ™]CGCCCGGCGGGCGCGGCG CAG[BHQ1]TGTTGGTTGTGAGTTG ATACTG (SEQ ID NO: 10) | | | |
| | | BRa07-R3 (Cy5 ™) | [Cy5 ™]CCGCGGGGCCCGCCCGGC GAC[BHQ2]AGCCGATCAGATAGAT CCCT (SEQ ID NO: 11) | | | |

1-2. Real-Time PCR Reaction

Using the designed primers, real-time PCR reaction was performed using the genomic DNA of each rice variety as a template.

Each genomic fragment including a target nucleic acid SNP to be identified was subjected to PCR amplification using 10 to 50 ng of genomic DNA as a template. A reaction mix having a total volume of 15 μl was prepared, including 7.5 μl of 2× PCR for rice variety identification, 1 μl of template DNA (5 to 10 ng/μl), 1 μl of FMMA probe (0.1 to 1.0 pmole/μl) for rice variety identification, 1 μl of primer (0.5-4.0 pmole/μl), and 4 μl of sterile water.

The reaction mix was activated at 95° C. for 15 minutes, and then subjected to 5 cycles, each consisting of 95° C. for 20 sec, 65° C. for 10 sec and 61° C. for 30 sec, followed by 30 cycles, each consisting of 95° C. for 20 sec and 63° C. for 30 sec.

As real-time PCR systems, CFX96™ (Biorad) and a MIC qPCR cycler (Bio Molecular System) were used. Fluorescence was measured in real time. Melting curve analysis was performed by measuring fluorescence while performing PCR under the following conditions: initial denaturation at 95° C. for 20 sec, and then hybridization at 45° C. for 30 sec, followed by heating from 65° C. to 99° C. at a rate of 0.4° C./sec.

1-3. Analysis of PCR Product Using Real-Time PCR and Final Determination

Figure 3:
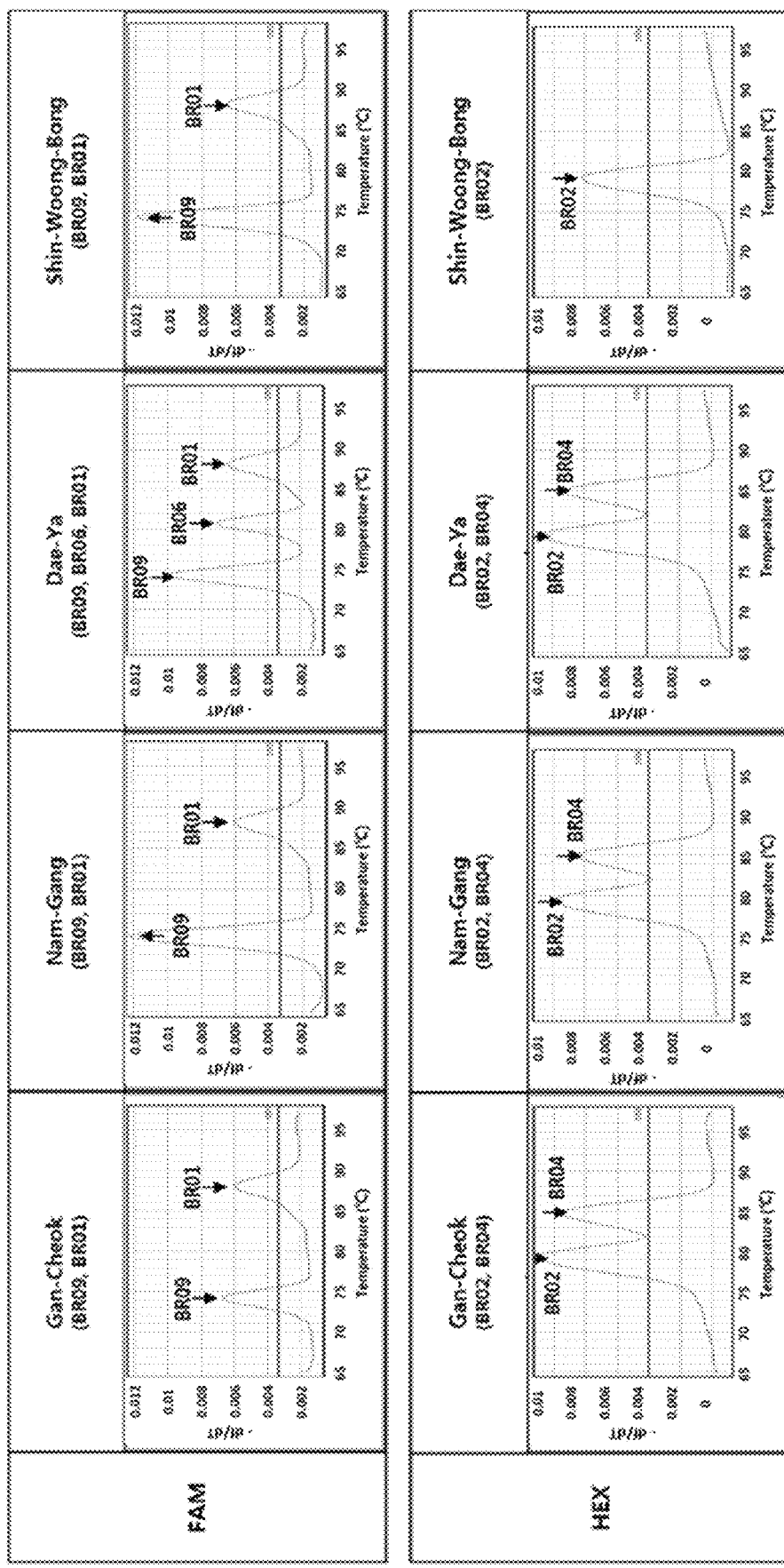
FIG. 3 shows the results of a rice variety identification experiment performed using allele-specific FMMA in an Example.

As a result of performing allele-specific FMMA on rice varieties such as Gan-Cheok, Nam-Gang, Dae-Ya and Shin-Woong-Bong, the presence of five genetic markers (BR01, BR02, BR04, BR06, and BR09) was identified by a single reaction using two fluorescent labels (FAM™ and HEX™). As a result, as shown in FIG. 3, it was possible to obtain a genotyping result corresponding to each rice variety. It was confirmed that it is possible to analyze multiple alleles in a single reaction using two or three different amplification product melting temperatures for each fluorescence channel.

Example 2

Rice Variety Identification Using Allele-Specific FMMA

Allele-specific FMMA for 20 gene markers used for rice variety identification was designed, and identification tests for 4 rice varieties were performed. Four fluorescence channels (FAM™, HEX™ TEXAS RED®, and CY5™) were used to enable analysis of 10 markers per test set, and the melting temperature was distributed to enable analysis of 2 or 3 markers for each fluorescence channel. Twenty genetic markers were analyzed using two sets capable of analyzing 10 genetic markers, respectively, and the results are shown in FIGS. 4 and 5.

Figure 4:
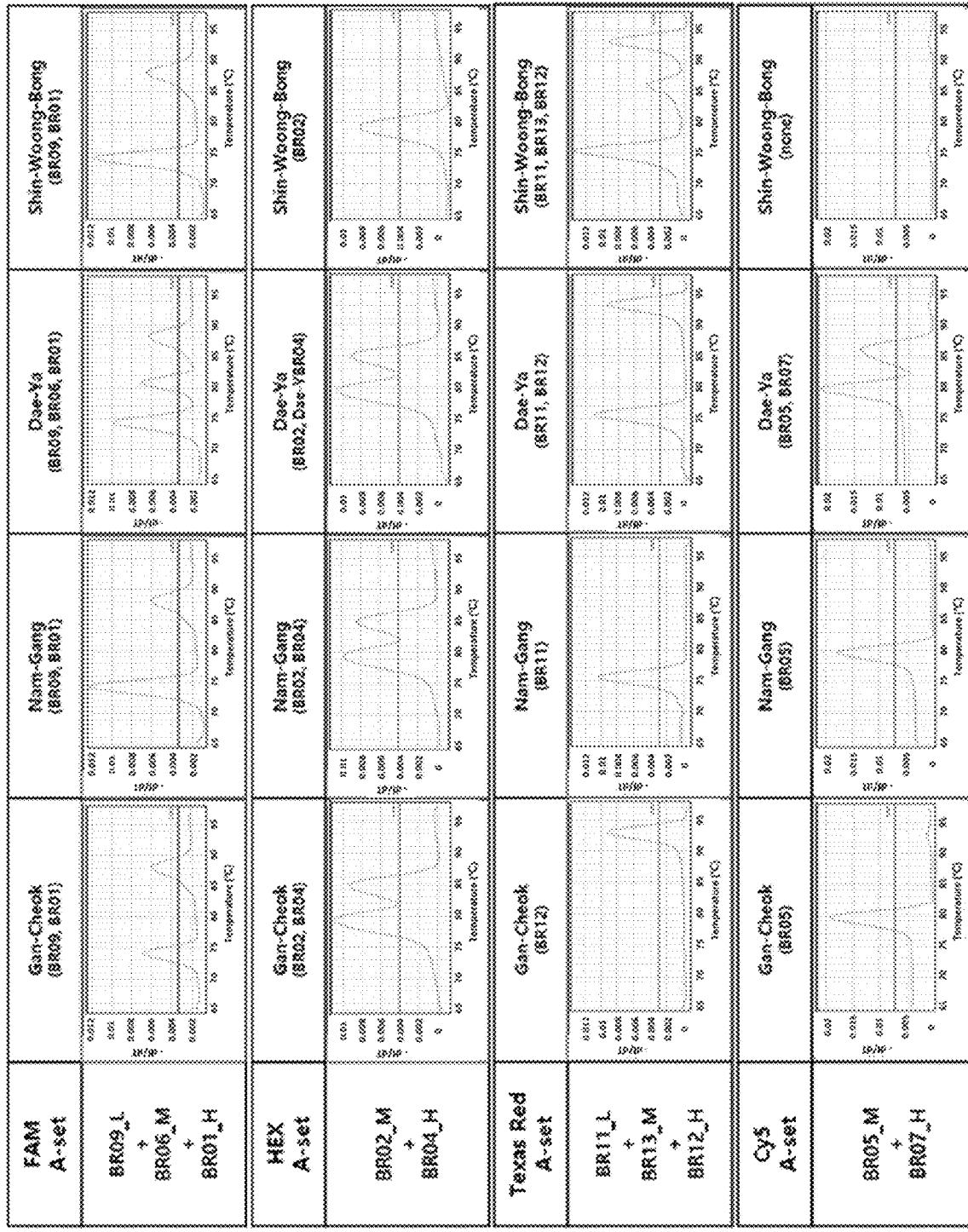
FIG. 4 shows the results of rice variety identification (set A) performed using allele-specific FMMA in an Example of the present invention.
Figure 5:
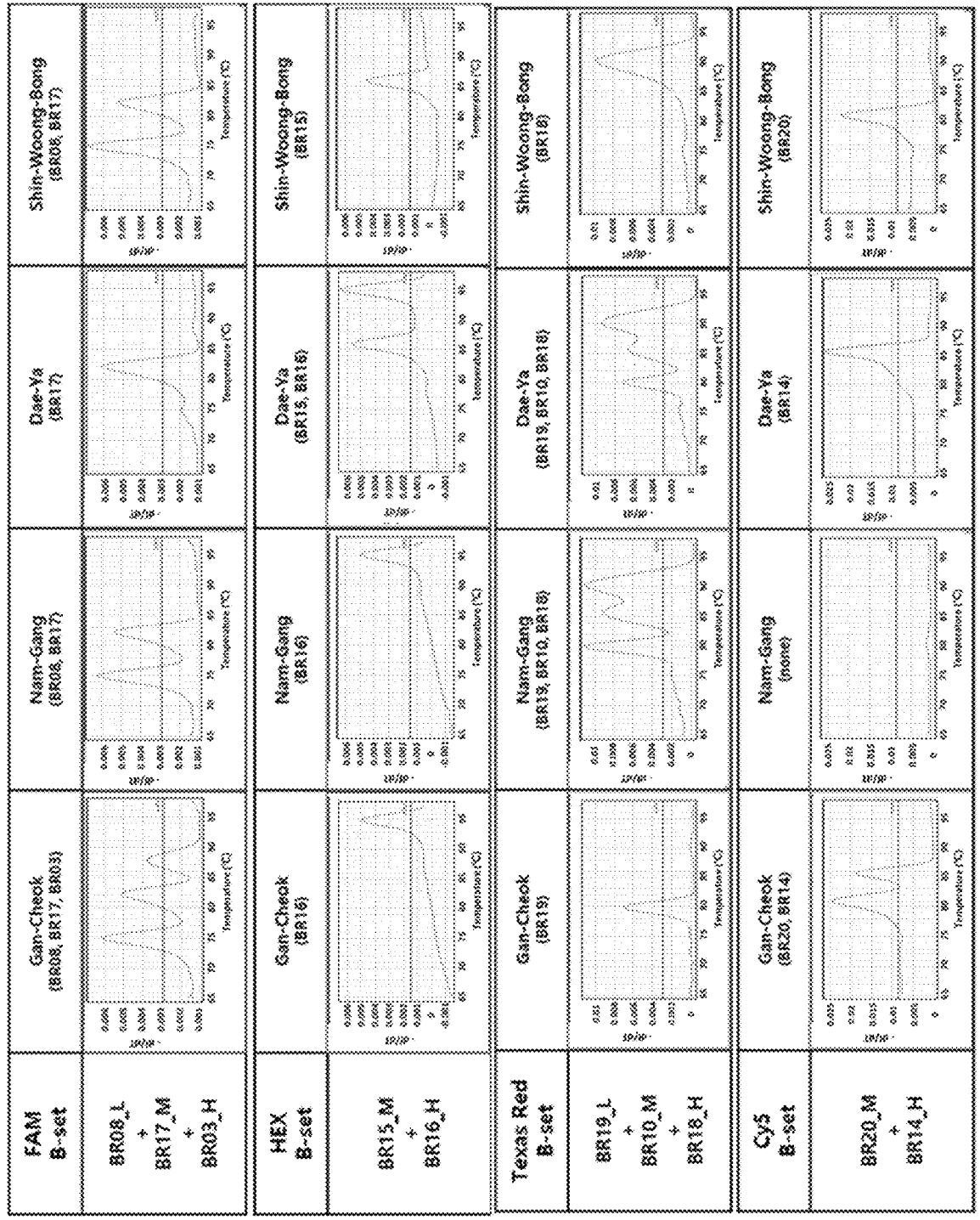
FIG. 5 shows the results of rice variety identification (set B) performed using allele-specific FMMA in an Example of the present invention.

As can be seen from the results in FIGS. 4 and 5, it was confirmed that the DNA extracted from the sample rice was specifically amplified in the marker set for rice variety identification, indicating that the sample rice was correctly identified to meet variety identification requirements. From this result, it was confirmed that multiple alleles can be analyzed in a single reaction by using two or three different amplification product melting temperatures for each fluorescence channel.

In conclusion, it was confirmed that the use of the FMMA method according to the present invention can simultaneously analyze 10 or more samples in a single reaction. This method can be applied not only for the determination of the presence or absence of allelic markers as performed in the Example above, but also for the determination of the presence or absence of multiple target nucleic acid genes, and there is no significant difference between the methods for determination. Thus, the method of the present invention can be applied to multiplex detection methods such as simultaneous diagnosis of infection with various pathogens.

Example 3

Analysis of Melting Temperature Distribution Depending on Length of Nucleic Acid Amplification Product In order to analyze multiple markers in a single fluorescence channel as in Example 1, it is necessary to distribute the melting temperature appropriately between the markers. In order to understand factors that influence the determination of the melting temperature, the correlation between the length of the amplification product and the melting temperature thereof was examined. The fluorescently labeled primer was fixed, and the length of the product was adjusted by changing the position of the reverse primer, and the melting temperature was analyzed. That is, as the 5' end fluorescent primer, the same primer was used, and as the 3' end primer, a primer having an adjusted length was used so that the length of the amplification product would vary between 50 bp and 350 bp. The primers used are shown in Table 3 below.

TABLE 3

|  | Name | Nucleotide sequence | PCR product size (bp) | PCR product $T_m$ (° C.) |
|---|---|---|---|---|
| BR05 | BRq05-F2 | CAATGTGGATTGTGAAGGTGA (SEQ ID NO: 12) | 102 | 79 |
|  | BRq05-F1 | GTTCAAGAATTTGGAGAATCAAT (SEQ ID NO: 13) | 121 | 79.5 |
|  | BRq05-F | GCAACATCGGACTGAAAGGT (SEQ ID NO: 14) | 170 | 81 |
|  | BRm05-F(200) | CTGTAAAGATTGAACTGCCAAAT (SEQ ID NO: 15) | 220 | 77/82 |
|  | BRc05-F | GGAACCACCACCGTTTAAATAA (SEQ ID NO: 16) | 278 | 82 |
|  | BRm05-F(341) | TGGTATGTCACATTCTGTACGA (SEQ ID NO: 17) | 362 | 82 |
|  | BRa05-R(CY5 ™) | [CY5 ™]GGAGACATCAGATACAGAGTG [BHQ2]TCGGTTATTGCAGGTGATaTTT (SEQ ID NO: 18) |  |  |
| BR13 | BRa13-F (TEXAS RED ®) | [TEXAS RED ®]CCGTACCTTAGAGAC AGCGTG[BHQ2]GATGCTTGCAAGAGGG GATaTT (SEQ ID NO: 19) |  |  |
|  | BRm13-R(70) | TCTTGATATGGCACCCATCCA (SEQ ID NO: 20) | 91 | 83.5 |
|  | BRm13-R(122) | CAGTCATTGGGGTCAATGCCA (SEQ ID NO: 21) | 143 | 85 |
|  | BRq13-R | GCAAGAACCAGGACCATGTGCT (SEQ ID NO: 22) | 208 | 85.5 |
|  | BRm13-R(247) | TGTCAGTCATGATAATCCAAGG (SEQ ID NO: 23) | 268 | 85.5 |
|  | BRm13-R(309) | CATGTTTAGAAACTGCAATGGC (SEQ ID NO: 24) | 330 | 85.5 |
| BR15 | BRa15-F2-1 (HEX ™) | [HEX]CGTCAGGTAAGCGTGACGACT [BHQ1]GACGTCATAGCAACAACtaCG (SEQ ID NO: 25) |  |  |
|  | BRm15-R(51) | CACCAACTCATCTTACCTTTAAC (SEQ ID NO: 26) | 72 | 80.5 |
|  | BRm15-R(102) | CAGAAGGTGCCCATCCATGTT (SEQ ID NO: 27) | 123 | 84.5 |
|  | BRm15-R(151) | CTACACCTACTTTCTTCGTCAA (SEQ ID NO: 28) | 172 | 84 |
|  | BRm15-R(204) | TAAGGGACATGACGGGTCAG (SEQ ID NO: 29) | 225 | 85.5 |
|  | BRq15-R | TGTCTGCACTGACTTCTTCATC (SEQ ID NO: 30) | 275 | 85.5 |
|  | BRm15-R(302) | ATCCATCATCCGAAGGATGTG (SEQ ID NO: 31) | 324 | 85.5 |
| BR20 | BRa20-F (CY5 ™) | [CY5 ™]GGAGACATCAGATACAGAGTG [BHQ2]ACTAGAATATGGAACCCTaGAG (SEQ ID NO: 32) |  |  |
|  | BRm20-R(52) | TGCTAGTACAGATGAGGAGGT (SEQ ID NO: 33) | 73 | 77.5 |
|  | BRq20-R1 | TTCAACATGCATGATGCAAAGC (SEQ ID NO: 34) | 144 | 80 |
|  | BRm20-R(183) | CGACATTCTTGTTTGATATTCTT (SEQ ID NO: 35) | 204 | 80.5 |
|  | BRq20-R | GATGAAGGATCTTGGTGTTGCT (SEQ ID NO: 36) | 260 | 81 |
|  | BRm20-R(313) | GATGATATGCTGATTGCTGCC (SEQ ID NO: 37) | 334 | 81 |

Figure 6:
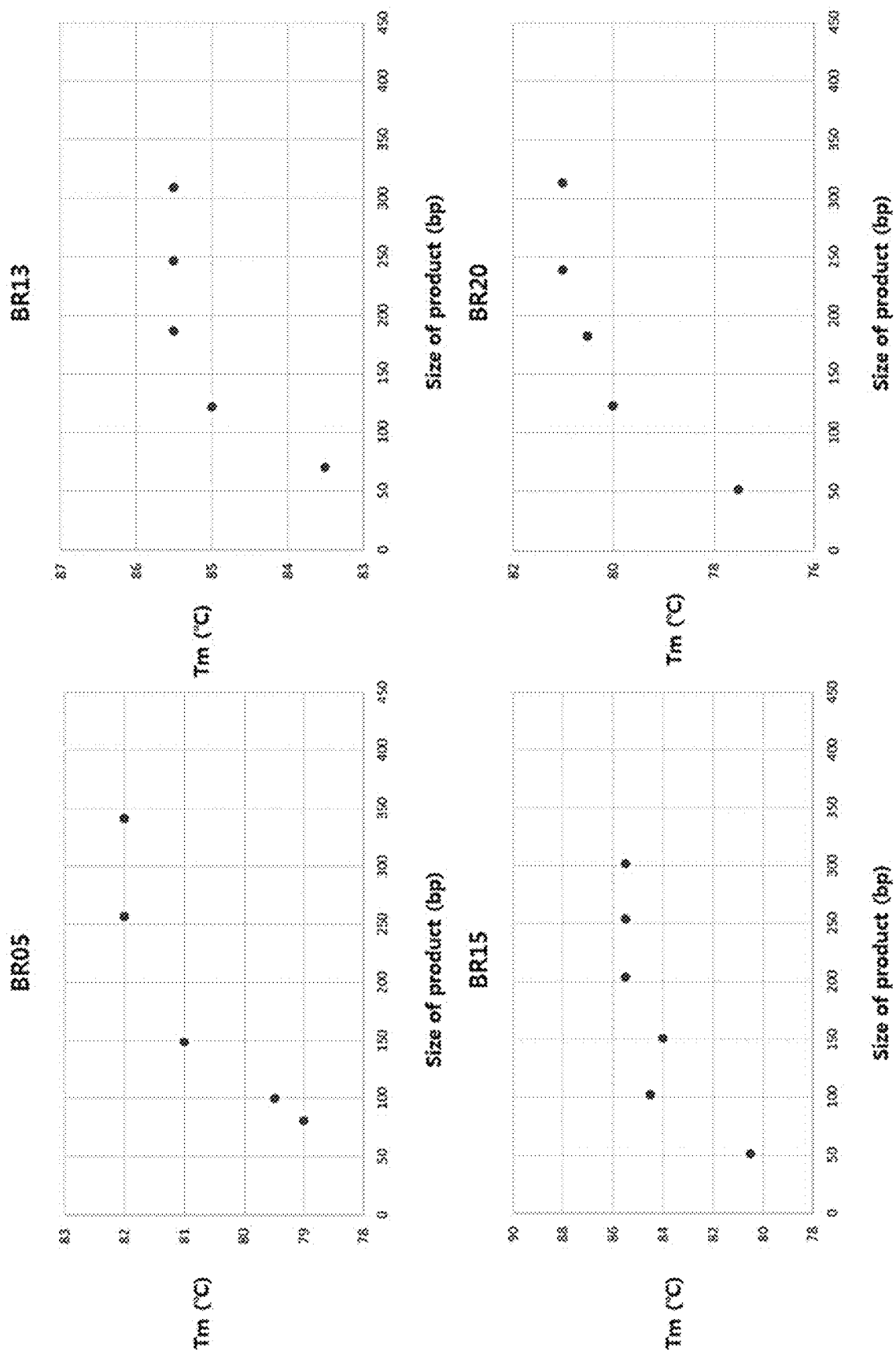
FIG. 6 shows the results of analyzing the melting temperature distribution of an amplification product depending on the length thereof in Example 4.

For four rice variety genetic markers (BR05, BR13, BR15 and BR20), changes in the melting temperatures of amplification products depending on the lengths thereof were tested, and the results are shown in FIG. 6. Referring to FIG. 6, it was observed that the melting temperature of the PCR amplification product increased as the length of the PCR amplification product increased. However, it could be seen that, when the length of the amplification product exceeded 200 or 250 bp, the effect thereof on the increase in the melting temperature was negligible. In conclusion, it was confirmed that the change in the melting temperature of the amplification product could be induced by controlling the length of the amplification product between 50 bp and 250 bp.

Example 4

Analysis of Melting Temperature Distribution on Length of Nucleic Acid Amplification Product and GC Content Among factors that influence melting temperature, the correlation between the GC content of the melting temperature control sequence used and the melting temperature of the entire amplification product was analyzed.

For three rice variety genetic markers (BR12, BR16, and BR20), the positions of the 5' and 3' end primers on the target nucleic acid gene were fixed, and the GC content of the melting temperature control sequence of the 5' end primer was set to two types (high and low GC %). The primers used are shown in Table 4 below. Under these conditions, analysis was performed, and the results are shown in FIG. 7.

TABLE 4

| Marker | Primer | Nucleotide sequence | GC% of Tm control sequence |
|---|---|---|---|
| BR12 | BRa12-F2_Hi (TEXAS RED ®) | [TEXAS RED ®]GCGGGCCGCGGGCGCCGCCAC [BHQ2]TCGACGGCGACCTGACTTGT (SEQ ID NO: 38) | 95.238 |
|  | BRa12-F2_Lo (TEXAS RED ®) | [TEXAS RED ®]GGAGACATCAGATACAGAGTG [BHQ2]TCGACGGCGACCTGACTTGT (SEQ ID NO: 39) | 47.619 |
|  | BR12-R | GCATTGGAGACGAACTGACG (SEQ ID NO: 40) |  |
| BR16 | BR16-F | TGGCGGGCGGGAGACGTTC (SEQ ID NO: 41) |  |
|  | BRa16-R3_Lo [HEX ™] | [HEX ™]GGAGACATTAGATATAGAGTG[BHQ1] ACTGGCTTGCTGCCGTATCCA (SEQ ID NO: 42) | 38.095 |
|  | BRa16-R3_Hi [HEX ™] | [HEX ™]CGCCCGGCGGGCGCGGCGCAG[BHQ1] ACTGGCTTGCTGCCGTATCCA (SEQ ID NO: 43) | 92.238 |
| BR20 | BRa20-F_Hi (CY5 ™) | [CY5 ™]GCGGGCCGCGGGCGCCGCCAC[BHQ2] ACTAGAATATGGAACCCTAGAG (SEQ ID NO: 44) | 47.619 |
|  | BRa20-F_Lo (CY5 ™) | [CY5 ™]GGAGACATCAGATACAGAGTG[BHQ2] ACTAGAATATGGAACCCTAGAG (SEQ ID NO: 32) | 95.238 |
|  | BRm20-R | TGCTAGTACAGATGAGGAGGT (SEQ ID NO: 33) |  |

Figure 7:
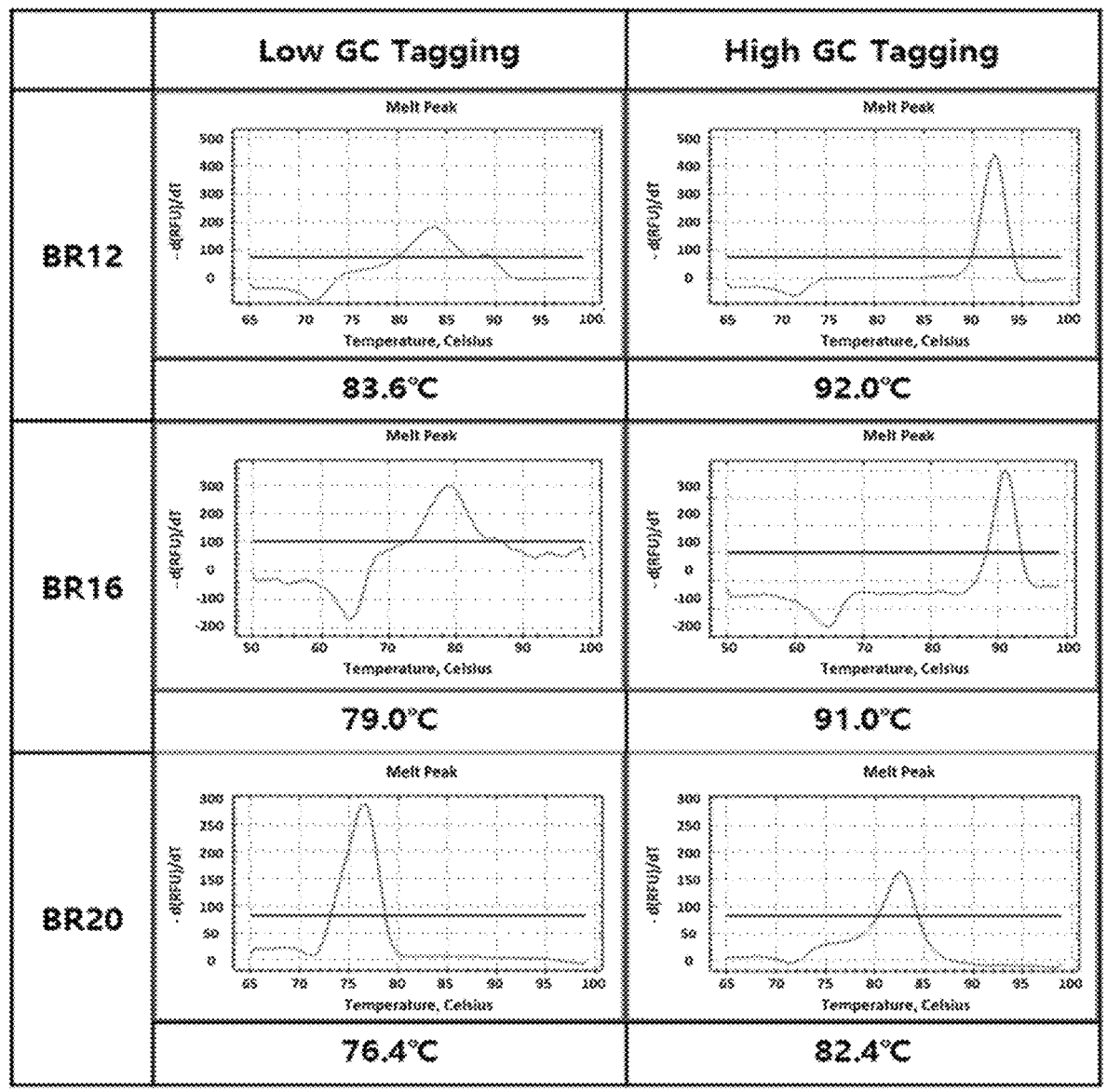
FIG. 7 graphically shows the correlation between the GC content of a melting temperature control sequence (T) and the melting temperature of the entire PCR product.

Referring to FIG. 7, it was confirmed that, when the GC content of the melting temperature control sequence was high, the melting temperature ($T_m$) of the amplification product increased compared to when the GC content of the melting temperature control sequence was low, even if the same primer was used. That is, it could be confirmed that, as the GC content of the melting temperature control sequence increased, the melting temperature of the entire amplification product increased.

Taking the results of Examples 3 and 4 together, it was confirmed that the melting temperature of the entire amplification product was influenced by a combination of the length of the amplification product and the GC content of the melting temperature control sequence used.

INDUSTRIAL APPLICABILITY

The use of the FMMA method of the present invention makes it possible to detect multiple targets simultaneously in a single reaction. Therefore, the method of the present invention may be widely used in the companion diagnostic field in which multiple target nucleic acid genes need to be analyzed, the agricultural and livestock field in which multiple alleles need to be analyzed, and the clinical pathology field in which multiple infectious agents need to be analyzed simultaneously.

Although the present invention has been described in detail with reference to embodiments, these embodiments are for illustrative purposes only and the scope of the present invention is not limited to these embodiments. Those skilled in the art will appreciate that various modifications and changes are possible without departing from the spirit and scope of the present invention, and such modifications and changes also fall within the scope of the present invention. Therefore, the true scope of the present invention should be defined by the appended claims and equivalents thereto.

The invention claimed is:

1. A method for multiplex analysis of amplification products, the method including steps of:
   a) preparing target-specific fluorescence-based multiple melting analysis (FMMA) probe/primer sets which each include an FMMA probe and a non-labeled primer, said FMMA probe having a linear structure of 5'-R-T-Q-C-3', wherein R is a fluorescent label, T is a melting temperature control sequence for inducing different temperatures of different amplification products, Q is a quencher, and C is a sequence complementary to a target nucleic acid sequence, and wherein each FMMA probe/primer is designed to produce each amplification product having a different melting temperature;
   b) amplifying multiple target nucleic acids in a sample containing one or more target nucleic acids by a nucleic acid polymerase chain reaction alone using the target-specific FMNMA probe/primer sets obtained in step a) to produce an amplification reaction product comprising a first amplification product with a first melting point and a second amplification product with a second melting point, wherein the first melting point and the second melting point differ from each other; and
   c) performing a melting temperature analysis on the first and the second amplification products.

2. The method of claim 1, wherein adjustment of the melting temperature of each FMMA probe/primer in the target-specific FMMA probe/primer sets is designed such that the first and the second melting points of the first and the second amplification products differ from each other by adjusting a length and a GC content of the amplification product and a length and a GC content of the melting temperature control sequence.

3. The method of claim 1, wherein the FMMA probes/primer sets are configured such that a difference between the first melting temperatures of the first amplification products and the second melting temperature of the second amplification product is 2° C. or higher.

4. The method of claim 3, wherein the FMMA probes/primer sets are configured such that the difference between the first melting temperature of the first amplification products and the second melting temperature of the second amplification product is 4° C. or higher.

5. The method of claim 1, wherein the melting temperature control sequence (T) of each of the probe/primer sets is 10 to 30 bp in length, and the first and the second amplification products are each 50 to 300 bp in length.

6. The method of claim 1, wherein the step (c) of performing melting temperature analysis comprises steps of:
   obtaining a melting curve by measuring a fluorescence generated by melting the amplification reaction product while increasing a temperature thereof; and
   obtaining a melting peak curve from the melting curve.

7. The method of claim 1, wherein the nucleic acid polymerase is an RNA-dependent RNA-polymerase, an RNA-dependent DNA-polymerase, a DNA-polymerase, or an RNA-polymerase.

8. The method of claim 7, wherein the DNA polymerase is selected from the group consisting of Taq polymerase, Tth polymerase, Tli polymerase, Pfu polymerase, Pwo polymerase, Bst polymerase, Sac polymerase, Tac polymerase, Tfl/Tub polymerase, Tru polymerase, Tne polymerase, Tma polymerase, Tsp polymerase, Mth polymerase, Phi29 polymerase, Klenow polymerase, T7 polymerase, and KOD DNA polymerase.

9. The method of claim 1, wherein the amplification product has a melting temperature of 50° C. to 100° C.

10. The method of claim 9, wherein the amplification product has a melting temperature of 60° C. to 95° C.

11. A kit for multiplex detection of target nucleic acids, the kit being based on the method of claim 1 and comprising the target-specific FMMA probe/primer sets of claim 1.

12. A kit for identification of allele-specific rice varieties, the kit being based on the method of claim 1 and comprising the target-specific FMMA probe/primer sets of claim 1.

* * * * *

UNITED STATES PATENT AND TRADEMARK OFFICE
CERTIFICATE OF CORRECTION

| | | |
|---|---|---|
| PATENT NO. | : 12,209,272 B2 | Page 1 of 1 |
| APPLICATION NO. | : 17/182705 | |
| DATED | : January 28, 2025 | |
| INVENTOR(S) | : Minsu Ko, Junsang Ko and Hyejeong Yeom | |

It is certified that error appears in the above-identified patent and that said Letters Patent is hereby corrected as shown below:

On the Title Page

After item (22)
Item (30) Foreign Application Priority Data, first column, please insert:
--Sept. 28, 2018 (KR) 10-2018-0116472-- therefor.

Signed and Sealed this
Eleventh Day of March, 2025

Coke Morgan Stewart
*Acting Director of the United States Patent and Trademark Office*